United States Patent [19]

Nyfors et al.

[11] Patent Number: 4,739,249
[45] Date of Patent: Apr. 19, 1988

[54] METHOD AND APPARATUS FOR THE MEASUREMENT OF THE PROPERTIES OF SHEET- OR FOIL-LIKE MATERIALS OF LOW ELECTRICAL CONDUCTIVITY

[75] Inventors: Ebbe G. Nyfors, Espoo; Pertt-Veli Vainikainen; Matti T. Fischer, both of Helsinki, all of Finland

[73] Assignee: Imatran Voima Oy, Helsinki, Finland

[21] Appl. No.: 41,481

[22] Filed: Apr. 23, 1987

[51] Int. Cl.⁴ .......................... G01R 27/00; G01G 7/00
[52] U.S. Cl. .............................. 324/58.5 C; 324/58 C; 324/58.5 R; 73/73; 73/159
[58] Field of Search ................ 73/159, 73; 340/602, 340/665; 324/58 R, 58 C, 58 A, 58 B, 58.5 C, 58.5 A, 58.5 B, 58.5 R

[56] References Cited

U.S. PATENT DOCUMENTS

| | | | |
|---|---|---|---|
| 3,514,703 | 5/1970 | Soga | 324/58.5 C |
| 3,710,243 | 1/1973 | Keenan | 324/58.5 B |
| 3,810,004 | 5/1974 | Henoch | 324/58.5 R |
| 4,297,874 | 11/1981 | Sasaki | 324/58.5 C |
| 4,350,883 | 9/1982 | Lagarde | 324/58 C |
| 4,581,575 | 4/1986 | Osaki | 324/58.5 C |

FOREIGN PATENT DOCUMENTS

| | | | |
|---|---|---|---|
| 2134147 | 1/1972 | Fed. Rep. of Germany | 324/58.5 R |
| 2233045 | 1/1973 | Fed. Rep. of Germany | 324/58.5 B |

Primary Examiner—Reinhard J. Eisenzopf
Assistant Examiner—Jose M. Solis
Attorney, Agent, or Firm—Birch, Stewart, Kolasch & Birch

[57] ABSTRACT

A measurement method and an apparatus are used for determining the moisture content of sheet- or foil-like materials (1) of high moisture content and low electrical conductivity. Ground planes (3) are adapted on both sides of the material (1) to be measured; between each ground plane (3) and the material (1) to be measured, at least one center conductor (2) is adapted approximately parallel to the material (1) to be measured in order to form a quasi-TEM transmission line resonator. Electromagnetic RF energy is fed into the quasi-TEM transmission line resonator so that the electromagnetic quasi-TEM waves propagate in the plane of the material (1) to be measured. The resonator supports for the transverse and longitudinal waves such resonant modes whose resonant frequencies and Q's are dependent on the properties of the material (1) to be measured. The resonant frequencies and related Q's are measured, and these are used for determining the complex dielectric constant of the material (1) to be measured or, alternatively, the characteristics related to them.

6 Claims, 3 Drawing Sheets

METHOD AND APPARATUS FOR THE MEASUREMENT OF THE PROPERTIES OF SHEET- OR FOIL-LIKE MATERIALS OF LOW ELECTRICAL CONDUCTIVITY

BACKGROUND OF THE INVENTION

1. Field of the Invention

The present invention concerns a method for determining the properties of planar or foil-like materials of high moisture content and low electrical conductivity.

The invention also involves an apparatus for the implementation of the method.

2. Description of Background Art

The application of conventional measurement equipment in the determination of properties of sheet- and foil-like materials moving rapidly on a production line is often difficult. The transducers used are mainly of a contacting type, such as humidity sensors for plywood, based on resistance measurement, or sheet basis weight measuring scales. Typically, the contacting transducers, e.g., capacitive sensors, are susceptible to a high measurement error by the vertical movement of the material. Transducers based on penetrating radiation, such as gamma rays, often have a slow response, are expensive, and, furthermore, are hazardous due to the ionizing radiation utilized. In contrast, a nonpenetrating radiation, such as infrared radiation, delivers only superficial information from the immediate surface of the material.

With the use of radio frequency radiation, many of the aforementioned drawbacks and sources of error can be eliminated. The noncontact measurement of material becomes feasible, and the measurement also conveys information about the inside of the material sheet. Due to the inexpensive construction of the transducer construction itself, several transducers can be advantageously mounted in a parallel arrangement, which facilitates a fast measurement across the entire line. Furthermore, by measuring a plurality of factors related to the propagation of radio waves in the material, a concurrent determination of material characteristics is possible. However, even when using RF transducers, the movement of the sheet or foil relative to the transducer often causes large errors in measurement since, in the measurement of thin sheets or foils, the transducer must be brought close enough to the material to obtain a sufficiently strong signal.

SUMMARY AND OBJECTS OF THE INVENTION

The aim of this invention is to overcome the drawbacks of the above described technique and to provide an entirely novel measurement method and apparatus for the determination of characteristics in sheet- or foil-like materials of low electrical conductivity and high moisture content.

The inventon is based on the principle that the transducer consists of parts located at both sides of the material, which together form an electromagnetic quasi-TEM transmission line resonator with several center conductors. Here, the construction supports several resonant wave modes, whose Q and resonant frequency are dependent on the material since its dielectric constant differs from that of air. By selecting an appropriate mode, these measurement signals can be maximized while the effect of material movement on the signals is minimized.

The invention provides appreciable benefits.

Consequently, the measurement method in accordance with the invention operating in the RF range, as well as the corresponding apparatus, can be used for concurrent determination of one or several properties of a sheet- or foil-like material. The material can be any material of low electrical conductivity, such as plywood sheet, plastic or cellulose sheet, or paper web. The material passes through the transducer without contacting it, which facilitates a rapid automatic measurement. Even relatively large displacements perpendicular to the the plane of the material sheet or foil do not appreciably affect the measurement result.

BRIEF DESCRIPTION OF THE DRAWINGS

In the following, the invention will be examined in more detail by means of exemplifying embodiments described in the attached figures.

DETAILED DESCRIPTION OF THE PREFERRED EMBODIMENTS

Transducers in accordance with the invention, which are applicable in the measurement of characteristics of sheet- or foil-like materials with low electrical conductivity, are shown in FIGS. 1-5. The transducer illustrated in the figures is comprised of two ground planes 3 and, in this example, of two center conductors 2 (strip, pipe, etc.) as well as insulator spacers 4 used for supporting the center conductors. The material 1 to be measured is located to the middle of the center conductors so that the material plane is parallel to the ground plane. The ground planes and the center conductors together form an electromagnetic resonator, in which the electromagnetic wave propagates parallel to the level of the material to be measured.

Figure 1:
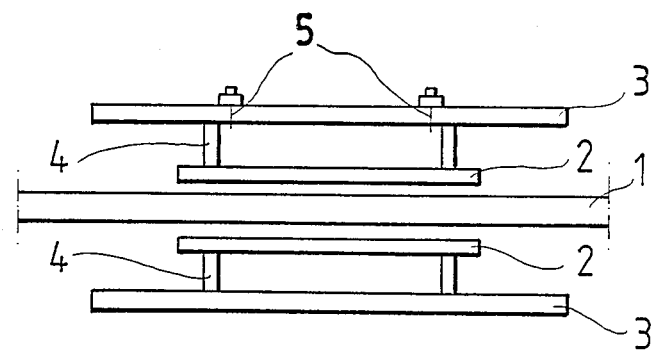
FIG. 1 shows a side view of a measurement transducer constructed of two ground planes, two center conductors, and isolating spacer supports.
Figure 2:
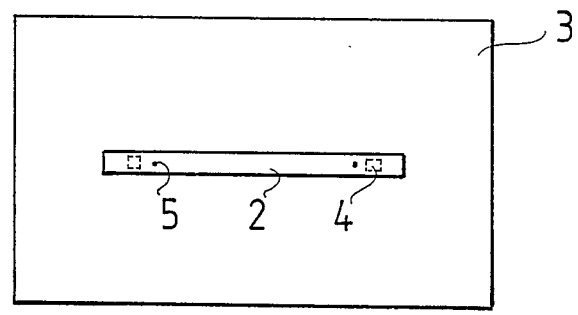
FIG. 2 shows a bottom view of a measurement transducer in accordance with FIG. 1.
Figure 3:
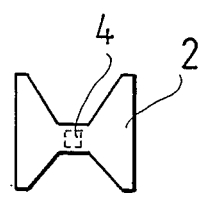
FIG. 3 shows a bottom view of the center conductor strip of a measurement transducer with a butterfly shape.

The resonator illustrated in FIGS. 1 and 2 is resonant when the wavelength is twice the length of the center conductors 2. The dielectric sheet between the center conductors 2 alters the wavelength and, consequently, also the resonant frequency of the construction. The material also attenuates the fields, which can be detected from the change of the resonator Q. Information from the characteristics of the resonance can be obtained by connecting the resonator to a measurement circuit via coupling pins or loops 5.

When the distance between the center conductors of the resonator in accordance with FIGS. 1-5 is increased without changing their spacing from the ground planes 3, the sensitivity of the transducer is reduced against the vertical displacements of the material 1 to be measured. However, the Q and the measurement sensitivity are then also decreased. By contrast, when the spacing of the center conductors 2 from the ground planes is increased without altering the mutual distance of the center conductors, the measurement sensitivity is increased while Q is decreased. The sensitivity to the vertical movement of material is not affected. A sufficient value for Q, which is about 500, is attained by choosing the spacings of the center conductors 2 to the ground planes 3 to be about 0.12 times the wavelength, and the mutual distance between the center conductors to be about 0.15 times the wavelength. Then, the measurement sensitivity provided by the transducer is relatively high, and its sensitivity to the vertical movement of the material is low.

Figure 4:
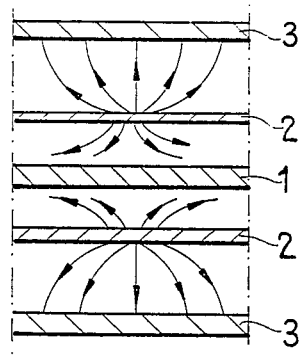
FIG. 4 shows the electrical field in the wave propagation direction for an even mode of a measurement resonator with two center conductors.

Quasi-TEM transmission line resonator with several center conductors, such as the resonator illustrated in FIGS. 1-5, support several resonant modes at different potential combinations of center conductors. In regard to the resonator with two center conductors, the situation can be described as the resonator supporting an even mode with the center conductors being equipotential and an odd mode with the center conductors having opposite potentials. Due to slightly different discontinuity capacitances, the resonant frequencies of the even and odd modes of same order are generally slightly displaced. Correspondingly, the field patterns are distinctly different in the plane orthogonal to the wave propagation direction of the even and odd resonant mode. The electric field pattern of the even mode is shown in FIG. 4, and the corresponding electric field pattern of the odd mode in FIG. 5. It can be seen in the figures that when the thin sheet or foil to be measured is located to the middle of the center conductors 2, the electric field at the location of the sheet to be measured is parallel to the plane of the sheet 1 while being orthogonal to the sheet 1 for the odd mode. Hence, the relative changes in the resonant frequency and Q of the resonator caused by the sheet to be measured, compared to the unloaded resonator, are distinctly higher with the even mode than with the odd mode.

Figure 6:
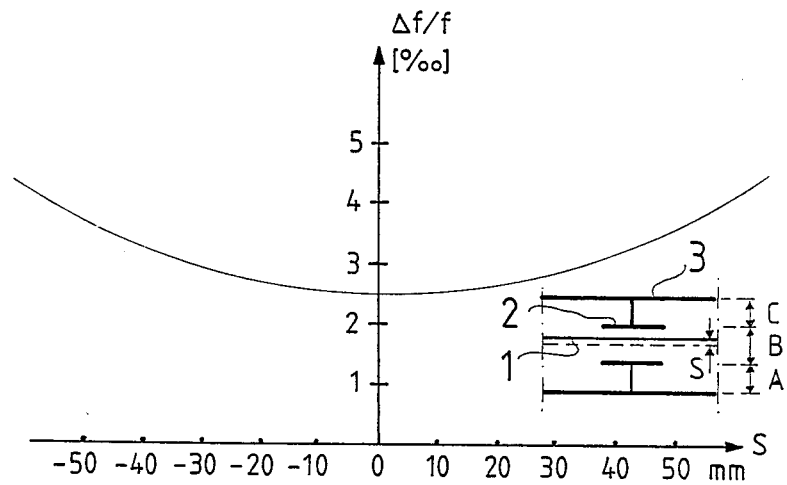
FIG. 6 shows the relative resonance frequency change of the measurement resonator in accordance with FIGS. 1-5 as a function of the plywood sheet position.

Furthermore, the change in measurement signals caused by the vertical movement of the sheet to be measured is distinctly smaller than with the odd mode. An example of this is illustrated in FIG. 6, in which the relative frequency change of the even mode is presented for a resonator in accordance with the invention, as compared to the change in the unloaded resonator when the plywood sheet in the resonator is moved vertically.

The vertical axis is the relative change of resonant frequency and the horizontal axis is the displacement of the sheet position from the midpoint of the transducer. The dimension A of the transducer shown in the figure is typically 100 mm, dimension B is 125 mm, and dimension C is 100 mm.

Figure 5:
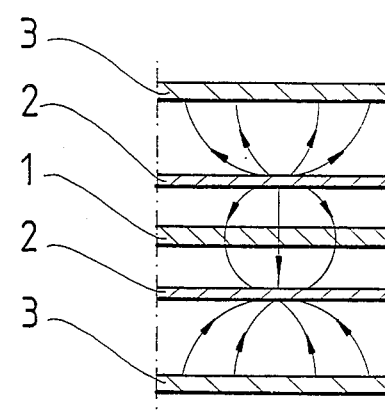
FIG. 5 shows the electrical field in the wave propagation direction for an odd mode of a measurement resonator with two center conductors.

To measure the moisture content of, for instance, a plywood sheet, the following approach can be applied. A measurement is performed using the resonator illustrated in FIGS. 1-5 in order to determine the change of resonant frequency and losses caused by the sheet, that is, the dielectric $Q_c$. It can be shown that the following equation is valid for the different resonant modes:

$$\frac{1/Q_c}{(f_o - f_1)/f_o} = \frac{c''}{(c')^n(c' - 1)}$$

where $f_o$ is the resonant frequency of the unloaded resonator, $f_1$ the resonant frequency with the sheet inserted between the center conductors as indicated by FIGS. 4 and 5, $c'$ is the real part of the sheet dielectric constant, and $c''$ is the imaginary part of the sheet dielectric constant. Constant n is 0 for the even mode and 1 for the odd mode. Consequently, the parameter calculated from the left side of the equation is not dependent on the thickness of the material sheet, such as plywood. Furthermore, the parameter is generally dependent only to a minor extent on the material density. However, the parameter is dependent on the moisture content of the material, e.g., wood, which offers a method for determining the moisture content. The equation also shows that by measuring a parameter of the left side for both the even (n=0) and the odd (n=1) mode, and by further calculating the ratio of these parameters, the real part of the dielectric constant of the material sheet or foil is obtained. By again using either of the parameters obtained for the different resonant modes, the imaginary part of the dielectric constant is also determined with neither result being dependent on the thickness of sheet to be measured.

Both the resonant frequency and the measurement range of the transducer can be influenced by the shape of the center conductors 2 of the resonator. For instance, a star center conductor with a butterfly-shaped cross section in accordance with FIG. 3 results in a resonant frequency which is half that of a strip-shaped center conductor with the same length. The lower resonant frequency allows, for instance, a wider distance between the center conductors, resulting in lower sensitivity to the vertical movement of the material. The measurement area of the transducer extends outside the edges of the center conductors to a distance approximately one-third of the mutual distance between the center conductors, thus resulting in a shorter and wider area of measurement for the butterfly-shaped center conductors compared to the strip-shaped center conductors of constant width. The center conductors 2 illustrated in FIGS. 1-5 are electrically open-circuited at both ends. However, the center conductors 2 can be short-circuited at both ends or at either end to the ground plane 3 without significantly altering their operation. The ground planes 3 must extend in the cross direction by at least a third-wavelength outside the edges of the center conductors to prevent radiation from the resonator.

Using conventional techniques, the resonant frequency and Q can be measured at least 50 times a second, which facilitates the determination of properties in a relatively fast moving material. By shaping the center conductors described in the foregoing, the measurement area of the transducer can be influenced, facilitating a focused determination of material properties. The facilities are important, for instance, in determining moisture content in plywood sheets because the sheet is thin; when dry, its dielectric constant is close to that of air; and after drying, the sheet is often extremely undulated. Furthermore, considering that the transfer speed of the sheet on the production line is relatively high, up to 3 m/s, and information on the moisture content is desired at a resolution of $30 \times 30$ cm$^2$ across the entire 1.5 m width of the line, a measurement rate of the aforementioned 50 measurement per second may be required.

More specifically, the method in accordance with the invention is characterized by what is stated in the characterizing part of claims 1 and 2, and, furthermore, the apparatus in accordance with the invention is characterized by what is stated in the characterizing part of claim 3.

Figure 7:
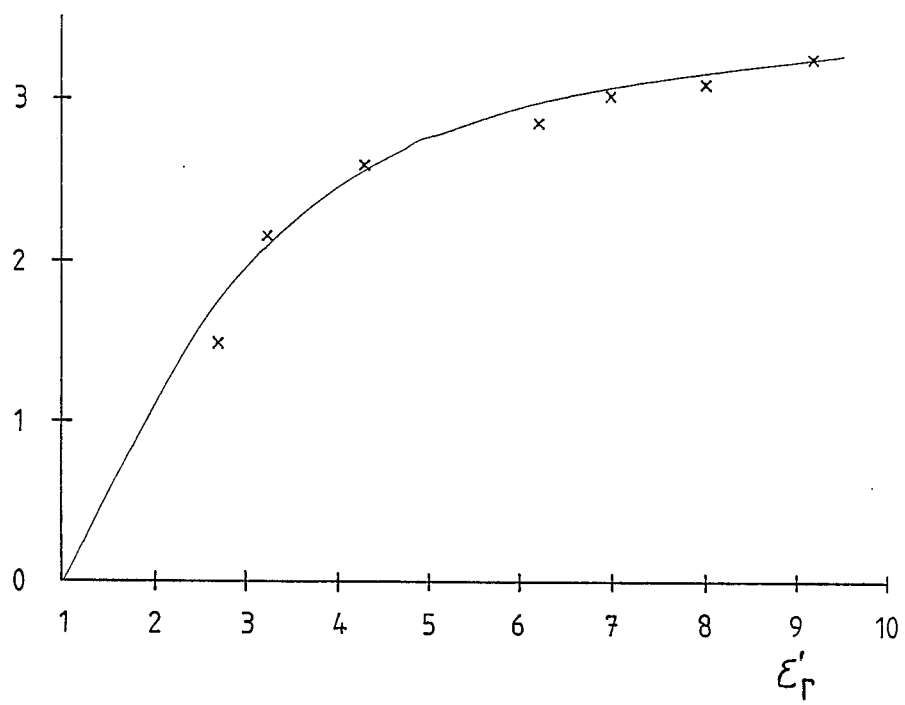
FIG. 7 shows in a graph form the relative frequency change of the odd resonant mode as a function of the dielectric coefficient.

The changes in resonant frequency caused by the material 1 to be measured, are different for the different resonant modes. Thus, the frequency change for the even mode is directly proportional to the parameter $c_r-1$, and for the odd mode, to the parameter $(c_r-1)/c'_r$ (refer to FIG. 7). When the moisture content in the material 1 to be measured is high, the real part of the dielectric constant $c'_r$ is also high. Then, according to the foregoing equation, small changes in moisture content of the wet material 1 cause no significant frequency change for the odd mode. Since, by contrast, the resonant frequency change for the even mode is appreciable, the effect of error factors can be compensated for. Such error factors are, for instance, the vertical movement of the measured object 1 relative to the transducer, changes in the mutual distance between the center conductors 2, and dimensional changes of the transducer parts due to temperature changes. If the moisture content of the material to be measured is high and the variations in moisture content are small, the aforementioned measurement error can be reduced. To reduce the measurement errors, the resonant frequencies of both resonant modes can be measured simultaneously. Then, the different resonant modes can be distinguished in the measurement setup from the different resonant frequencies characteristic of the modes. The error compensation can be simply performed by subtracting the resonant frequencies of the modes from each other. However, the compensation is not complete because the effect of error sources on the resonant frequencies of the different modes is not equal. The effectiveness of compensation depends on how well the effect of the error sources can be arranged equal on the different resonant modes. By choosing the mutual distance between the center conductors 2 and the spacing of the ground planes 3 from the center conductors 2 appropriately, the effect of error sources can be decreased significantly. An example of this, error in measurement of paper moisture content was reduced to one-third by compensation when the distance between the center conductors 2 was chosen as 5 cm, and the spacing of the ground planes 3 from the center conductors 2 was chosen as 6 cm. The moisture content of paper was 58% on the average, and its variation range was ±2.5%-units.

In the application referred to in the foregoing, the measurement frequencies used were in the order of 350 MHz. Information from the characteristics of the resonance is obtained by feeding the RF signal to coupling pins 5 or corresponding coupling loops, and then measuring the resonant frequencies. The resonant frequencies are found by, for instance, sweeping over the frequency range of the resonator and then determining the amplitude maxima of the signal.

What is claimed is:

1. A measurement method for measuring the properties of sheet- or foil-like materials (1) of high moisture content and low electrical conductivity, characterized in that ground planes (3) are adapted to both sides of the material (1) to be measured, between each of the ground planes (3) and the material (1) to be measured is adapted at least one center conductor (2), approximately parallel to the material, in order to form a quasi-TEM transmission line resonator, the quasi-TEM transmission line resonator is fed with electromagnetic RF energy so that the quasi-TEM modes propagate parallel to the material (1) to be measured, and the resonator supports resonant modes of both transverse and longitudinal modes, whose resonant frequencies and Q's are dependent on the properties of the material (1) to be measured, the resonant frequencies and related Q's are measured, and these frequencies are used for determining by prior art methods the complex dielectric constant of the material (1) to be measured as well as the associated parameters.

2. A measurement method as claimed in claim 1, characterized in that only the resonant frequency and/or Q of the resonant mode parallel to the plane of the material (1) to be measured is measured in order to reduce errors caused by movement of the material (1) to be measured relative to the resonator and to improve the sensitivity of measurement.

3. A measurement method as claimed in claim 1, characterized in that the resonant frequencies of at least two resonant modes are measured, and the difference between at least two resonant frequencies is determined representing a moisture value proportional to that of the material to be measured.

4. An apparatus for measuring the properties of sheet- or foil-like materials (1) of high moisture content and low electrical conductivity, with the apparatus consisting of at least two ground planes (3), at least two center conductors (2) adapted between the ground planes (3) in order to form a quasi-TEM transmission line resonator, at least one coupling pin (5) for feeding electromagnetic RF energy into the resonator, characterized in that the material (1) to be measured is adapted to pass between the center conductors (2) so that the center conductors (2) are approximately parallel to the material (1) to be measured in order to impose transverse and longitudinal resonant modes on the material (1) to be measured.

5. An apparatus as claimed in claim 4, characterized in that the ground planes (3) enclosing the material (1) to be measured are planar and approximately parallel to the center conductors (2).

6. An apparatus as claimed in claim 4 or 5, characterized in that there are two center conductors (2).

* * * * *